(12) United States Patent
Hanhauser et al.

(10) Patent No.: US 11,726,015 B2
(45) Date of Patent: Aug. 15, 2023

(54) SYSTEM AND METHOD FOR PRESERVATION, TRANSPORT, AND ANALYSIS OF WATER SAMPLES

(71) Applicant: MASSACHUSETTS INSTITUTE OF TECHNOLOGY, Cambridge, MA (US)

(72) Inventors: Emily Hanhauser, Brookline, MA (US); Michael Bono, Somerville, MA (US); Anastasios John Hart, Waban, MA (US); Rohit Karnik, Cambridge, MA (US); Xiaoyuan Ren, Cambridge, MA (US); Chintan Vaishnav, Belmont, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 17/392,326

(22) Filed: Aug. 3, 2021

(65) Prior Publication Data

US 2021/0364398 A1    Nov. 25, 2021

Related U.S. Application Data

(62) Division of application No. 15/497,761, filed on Apr. 26, 2017, now Pat. No. 11,131,609.

(Continued)

(51) Int. Cl.
*G01N 1/40* (2006.01)
*G01N 1/10* (2006.01)
(Continued)

(52) U.S. Cl.
CPC ......... *G01N 1/405* (2013.01); *B01D 15/1892* (2013.01); *B01J 20/264* (2013.01);
(Continued)

(58) Field of Classification Search
CPC .... G01N 1/405; G01N 1/40; G01N 2001/005; G01N 1/4077; G01N 2001/4088;
(Continued)

(56) References Cited

U.S. PATENT DOCUMENTS 2,955,067 A    10/1960    McBurney et al.
3,245,882 A    4/1966    Guthrie
(Continued)

FOREIGN PATENT DOCUMENTS

WO    2010078404 A1    7/2010

OTHER PUBLICATIONS

F. Raposo, M.A. De La Rubia, R. Borja, Methylene blue number as useful indicator to evaluate the adsorptive capacity of granular activated carbon in batch mode: Influence of adsorbate/adsorbent mass ratio and particle size, Journal of Hazardous Materials, vol. 165, Issues 1-3, 2009, pp. 291-299 (Year: 2009).*

(Continued)

*Primary Examiner* — Eric S. McCall
*Assistant Examiner* — Timothy P Graves
(74) *Attorney, Agent, or Firm* — Gesmer Updegrove LLP

(57) ABSTRACT

A device for collecting contaminants from water samples is provided. The device includes a solid sorbent that collects and stores the contaminants from water samples. The solid sorbent is configured to allow for the preservation of the stored contaminants. The concentrations of the contaminants in the water samples are determined via analysis of the solid sorbent or via elution of the stored contaminants from the sorbent and analysis of the eluate solution.

23 Claims, 11 Drawing Sheets

Related U.S. Application Data

(60) Provisional application No. 62/327,503, filed on Apr. 26, 2016.

(51) Int. Cl.

| | | |
|---|---|---|
| *B01L 3/00* | (2006.01) | |
| *G01N 1/12* | (2006.01) | |
| *G01N 1/20* | (2006.01) | |
| *B01D 15/18* | (2006.01) | |
| *B01J 20/28* | (2006.01) | |
| *B01J 20/26* | (2006.01) | |
| *B01J 20/34* | (2006.01) | |
| *C02F 1/28* | (2023.01) | |
| *C02F 1/42* | (2023.01) | |
| *C12Q 1/6806* | (2018.01) | |
| *G01N 1/00* | (2006.01) | |
| *C02F 101/10* | (2006.01) | |
| *C02F 101/20* | (2006.01) | |

(52) U.S. Cl.
CPC ....... *B01J 20/2805* (2013.01); *B01J 20/3425* (2013.01); *B01L 3/5023* (2013.01); *C02F 1/281* (2013.01); *C02F 1/285* (2013.01); *C02F 1/42* (2013.01); *C12Q 1/6806* (2013.01); *G01N 1/10* (2013.01); *G01N 1/12* (2013.01); *G01N 1/20* (2013.01); *G01N 1/4055* (2013.01); *B01J 2220/00* (2013.01); *B01L 2200/028* (2013.01); *B01L 2200/0631* (2013.01); *B01L 2200/185* (2013.01); *B01L 2300/069* (2013.01); *B01L 2300/0627* (2013.01); *B01L 2300/12* (2013.01); *C02F 2101/103* (2013.01); *C02F 2101/20* (2013.01); *C02F 2303/16* (2013.01); *G01N 2001/005* (2013.01); *G01N 2001/4061* (2013.01)

(58) Field of Classification Search
CPC .......... G01N 21/51; G01N 30/00; G01N 1/10; G01N 1/12; G01N 1/20; G01N 1/4055; G01N 2001/4061; B32B 2266/128; C08J 2205/028; B01L 3/5023; B01L 2200/028; B01L 2200/0631; B01L 2200/185; B01L 2300/0627; B01L 2300/069; B01L 2300/12; B01D 15/1892; B01J 20/264; B01J 20/2805; B01J 20/3425; B01J 2220/00; C02F 1/281; C02F 1/285; C02F 1/42; C02F 2101/103; C02F 2101/20; C02F 2303/16; C12Q 1/6806

See application file for complete search history.

(56) References Cited

U.S. PATENT DOCUMENTS

| | | | |
|---|---|---|---|
| 6,986,818 | B2 | 1/2006 | Tillotson et al. |
| 9,358,534 | B2 | 6/2016 | Bono et al. |
| 2003/0215958 | A1* | 11/2003 | Kin .......... G01N 1/40 436/167 |
| 2005/0011831 | A1 | 1/2005 | Pawliszyn |
| 2005/0227269 | A1* | 10/2005 | Lloyd, Jr. .......... B01L 3/50825 435/6.1 |
| 2012/0222500 | A1* | 9/2012 | Riess ........... G01N 1/405 73/863.23 |
| 2012/0222555 | A1 | 9/2012 | Riess et al. |
| 2013/0313198 | A1* | 11/2013 | Giese ........... B01D 15/20 210/291 |

OTHER PUBLICATIONS

Office Action issued by Indian Patent Office Action dated Mar. 3, 2021 in related Indian Patent App. No. 201827043700.

International Search Report and Written Opinion issued in related PCT Application No. PCT/US2017/029614 dated Oct. 26, 2017.

Ezel Boyaci, "Sorption of as(V) From Waters by Use of Novel Amine-Containing Sorbents Prior to HGAAS and ICP-MS Determination." Izmir Institute of Technology. Jul. 2008.

Xiu-Ping Yan et al. "Flow Injection On-Line Sorption Preconcentration Coupled with Hydride Generation Atomic Fluorescence Spectrometry for Determination of (Ultra)trace Amounts of Arsentic(III) and Arsenic(V) in Natural Water Samples." Analytical Chemistry, vol. 74, No. 9, May 1, 2002. pp. 2162-2166.

Kikuo Terada et al. "Differential Preconcentration of Arsenic(III) and Arsenic(V) with Thionalide Loaded on Silica Gel." Analytica Chimico Acta, vol. 158, (1984). pp. 207-215.

A.G. Howard et al. "Selective Pre-concentration of Arsenite on Mercapto-modified Silica Gel." Analyst, vol. 112, Feb. 1987. pp. 159-162.

Daniel Chen et al. "Separation and preconcentration of inorganic arsenic species in natural water samples with 3-(2-aminoethylamino) propyltrimethoxysilane modified ordered mesoporous silica microcolumn and their determination by inductively coupled plasma optical emission spectrometery." Jornal of Hazardous Materials, vol. 164, (2009). pp. 1146-1151.

Sridhar Chinthakindi et al. "Iron oxide functionalzed graphene nano-composite for dispersive solid phase extraction of chemical warfare agents from aqueous samples." Journal of Chromatography A. vol. 1394, (2015). pp. 9-17.

Hasan Bagheri et al. Preparation and characterization of magnetic nanocomposite of Schiff base/silica/magnetite as a preconcentration phase for the trace determination of heavy metal ions in water, food and biological samples using aomic absorption spectrometry. Talanta, vol. 97, (2012). pp. 87-95.

Susan Sadeghi et al. "Surface modified magnetic Fe3O4 nanoparticles as a selective sorbent for solid phase extraction of uranyl ions from water samples." Journal of Hazardous Materials, (2012). pp. 208-216.

H. Parham et al. "Solid phase extraction-spectrophotometic determination of fluoride in water samples using magnetic iron oxide nanooparticles." Talanta. vol. 80, (2009). pp. 664-669.

Hooshang Parham et al. "Solid phase extraction-spectrophotometric determination of salicylic acid using magnetic iron oxide nanoparticles as extractor." Journal of Pharmaceutical and Biomedical Analysis, (2009). vol. 50. pp. 58-63.

Anna A. Karamani et. al. "Zero-valent iron/iron oxide-oxyhydroxide/ graphene as a magnetic sorbent for the enrichment of polychlorinated biphenyls, polyaromatic hydrocarbons and phthalates prior to gas chromatography-mass spectrometry." Journal of Chromatography A, vol. 1271, (2013). pp. 1-9.

Qiang Han et. al. "Facile and tunable fabrication of Fe3O4/graphene oxide nanocomposites and their application in the magnetic solid-phase extraction of polycyclic aromatic hydrocarbons from environmental water samples." Talanta, 101. (2012). pp. 388-395.

Alexander E. Gash et al. "New sol-gel synthetic route to transition and main-group metal oxide aerogels using inorganic salt precursors." Journal of Non-Crystalline Solids. vol. 285. (2001). pp. 22-28.

Stephen J. Juhl et al. "Epoxide-assisted alumina aerogels by rapid supercritical extraction." Journal of Non-Crystalline Solids. vol. 426. (2015). pp. 141-149.

Alexander E. Gash et al. "Use of Epoxides in the Sol-Gel Synthesis of Porous Iron(III) oxide Monoliths from Fe(III) Salts." American Chemical Society. vol. 13. (2001). pp. 999-1007.

William J. Campbell et al. Micro and Trace Analysis by a Combination of Ion Exchange Resin-Loaded Papers and X-Ray Spectrography. U.S. Department of the Interior, Bureau of Mines, College Park Metallurgy Research Center, College Park, MD. vol. 38. Jul. 1966. pp. 987-996.

Kaisa Vaaramaa et al. "Removal of metals and anions from drinking water by ion exchange." Desalination. vol. 155 (2003). pp. 157-170.

Erol Pehlivan et al. "Ion-exchange of Pb2, Cu2, Zn2+, Cd2+, Cd2+, and Ni2+ ions from aqueous solution by Lewatit CNP 80." Journal of Hazardous Materials. vol. 140. (2007) pp. 299-307.

(56) References Cited

OTHER PUBLICATIONS

Pietro Escobar Franco et al. Nickel(II) and zinc(II) removal using Amberlite IR-120 resin: Ion exchange equilibrium and kinetics. Chemical Engineering Journal. vol. 221 (2013). pp. 426-435.

Veronique Vacchina et al. "Use of dried blood spots and inductively coupled plasma mass spectrometry for multi-element determination in blood." Journal of Trace Elements in Medicine and Biology. Jul. 2014. vol. 28. pp. 255-259.

V. Michaud et al. "Long-term storage at tropical temperature of dried-blood filter papers for detection and genotyping of RNA and DNA viruses by direct PCR." Journal of Virologicial Methods. vol. 146. (2007). pp. 257-265.

S. Chaorattanakawee et al. "Storage Duration and Polymerase Chain Reaction Detection of Plasmodium Falciparum From Blood Spots on Filter Paper." American Journal of Tropical Medicine and Hygiene. vol. 69(1). (2003). pp. 42-44.

Saana Hokkanen et al. "A review on modification methods to cellulose-based adsorbents to improve adsorption capacity." Water Research. vol. 91. (2016) pp. 156-173.

Daisy Setyono et. al. "Functionalized paper—A readily accessible adsorbent for removal of dissolved heavy metal salts and nanaoparticles from water." Journal of Hazardous Materials. vol. 302. (2016) pp. 120-128.

S. Pitsari et al. "Enhanced lead adsorption by unbleached newspaper pulp modified with citric acid." Chemical Engineering Journal. vol. 223. (2013) pp. 18-30.

David William O'Connell et al. "Heavy metal adsorbents prepared from the modification of cellulose: A review." Bioresource Technology. vol. 99. (2008) pp. 6709-6724.

Mark M. Benjamin et al. "Sorption and Filtration of Metals Using Iron-Oxide-Coated Sand." Wat. Res. vol. 30(11) (1996). pp. 2609-2620.

Kai Zhang et al. "Graphene oxide/ferric hydroxide composites for efficient arsentate removal from drinking water." Journal of Hazardous Materials. vol. 182. (2010) pp. 162-168.

Jennifer A. Wilkie et al. "Adsorption of arsenic onto hydrous ferric oxide: effects of adsorbate/adsorbent ratios and co-occurring solutes." Colloids and Surfaces A: A Physicochemical and Engineering Aspects. vol. 107. (1996). pp. 97-110.

O.S. Thirunavukkarasu et al. "Arsenic Removal from Drinking Water using Iron Oxide-Coated Sand." Water, Air, and Soil Pollution. vol. 142. (2003). pp. 95-111.

Armindo Santos et al. "Synthesis and characterization of iron-PVA hydrogel microspheres and their use in the arsenic (V) removal from aqueous solution." Chemical Engineering Journal. vol. 210. (2012). pp. 432-443.

Liu Ruiping et al. "Arsenic removal through adsorption, sand filtration and ultrafiltration: In situ precipitated ferric and manganese binary oxides as adsorbents." Desalination. vol. 249. (2009). pp. 1233-1237.

Ismail M.M. Rahman et al. "Decontamination of spent iron-oxide coated sand from filters used in arsenic removal." Chemosphere. vol. 92. (2013). pp. 196-200.

Merve Donmez Oztel. et. al. "Arsenite removal by adsorption onto iron oxide-coated pumice and sepiolite." Environ Earth Science. vol. 73. (2015). pp. 4461-4471.

Tien Vinh Nguyen et. al. "Arsenic removal by iron oxide coated sponge: Experimental performance and mathematical models." vol. 182. (2010). pp. 723-729.

Mark S. H. Mak et al. "Zero-valent iron and iron oxide-coated sand as a combination for removal of co-present chromate and arsenate from groundwater with humic acid of co-present chromate and arsenate from groundwater with humic acid." Environmental Pollution. vol. 159. (2011). pp. 377-382.

Savasis Dixit et al. Comparison of Arsenic (V) and Arsenic (III) Sorption onto Iron Oxide Minerals: Implications for Arsenic Mobility. Environ Sci. Technol. vol. 37. (2003). pp. 4182-4189.

Eric Arifin et al. "Simple and Efficient Synthesis of Iron Oxide-Coated Silica Gel Adsorbents for Arsenic Removal: Adsorption Isotherms and Kinetic Study." Bull. Korean Chem. Soc. vol. 34 (8). (2013). pp. 2358-2366.

* cited by examiner

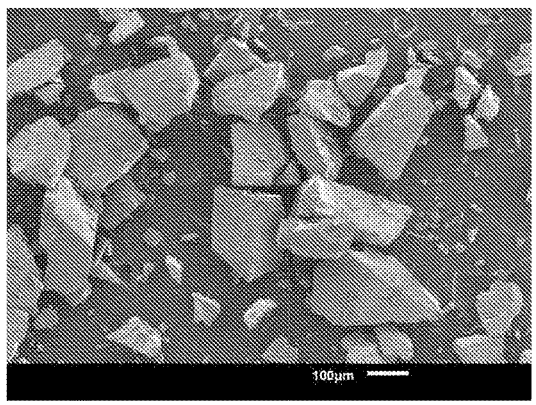 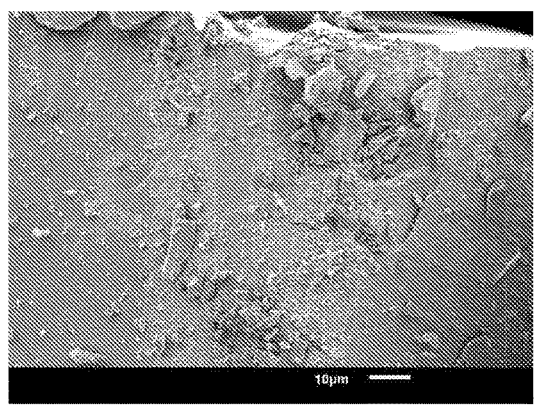
FIG. 6A                    FIG. 6B

| Tea bag # | 1 | 2 | 3 | 4 | 5 | 6 |
|---|---|---|---|---|---|---|
| Resin size (μm) | 650 | 650 | 650 | 300-400 | 650 | 650 |
| Bag mesh size (μm) | 400 | 300 | 150 | 150 | 400 | 400 |
| Bag shape | Rectangle | Rectangle | Rectangle | Rectangle | Long rectangle | Circle |

SYSTEM AND METHOD FOR PRESERVATION, TRANSPORT, AND ANALYSIS OF WATER SAMPLES

PRIORITY INFORMATION

This application is a divisional application of U.S. application Ser. No. 15/497,761 filed Apr. 26, 2017, which claims priority to U.S. Provisional Application No. 62/327,503 filed Apr. 26, 2016, the contents of which are incorporated herein by reference.

BACKGROUND OF THE INVENTION

The invention is related to the field of water quality monitoring, and in particular the invention describes technology to enable water samples to be preserved in a compact form that is suitable for storage and/or transport to centralized laboratories for chemical, microbial, or other analysis.

The safety of drinking water is judged by its physical, chemical, and microbial characteristics. Drinking water must be free of pathogens, contain low levels of toxic chemicals, and be tasteless, odorless, and colorless. Water quality is assessed in terms key parameters for biological contamination, where coliform bacteria is used as a proxy for fecal contamination; physical contamination, by use of parameters such as turbidity and pH; and chemical contamination, where acceptable limits are specified for contaminants such as arsenic, fluoride, nitrate, pesticides, and heavy metals such as lead, nickel, and copper. Many of these contaminants, such as arsenic and heavy metal contamination, occur naturally, whereas other contaminants such as nitrate and pesticides results from human activities.

Water quality monitoring is typically performed using field test kits, mobile/local laboratories, or more centralized government or commercial laboratories. Field tests provide rapid results with minimal training, but the accuracy, throughput, and sample processing ability in the field is limited. On the other hand, centralized laboratories are relatively expensive and often involve transportation of significant volumes (e.g. 250 to 1000 milliliters (mL)) of water over long distances to urban areas where these laboratories are located. This poses major difficulties on the ability to acquire water quality data. For example, field testing to quantify low levels (<100 micrograms per milliliter ($\mu g/mL$)) of arsenic contamination is cumbersome, and contaminants like mercury, lead, cyanide need to be analyzed in the laboratory. Testing for all the major types of pathogens is impossible in the field and even in the laboratory; instead, total coliform bacteria are measured as a proxy indicator of fecal contamination. Field tests provide positive/negative or semi-quantitative results, and testing in centralized laboratories is required for accurate analysis. These challenges place major limitations on the ability to acquire water quality data and involve considerable fieldwork.

Although similar problems of water quality exist in many other parts of the world, these challenges are exemplified in the case of India. India's drinking water problems are grave in terms of both availability as well as quality. While increasing the volume of water available for drinking and other domestic consumption is not the focus of this technology, it should be noted that according to India's National Rural Drinking Water Program (NRDWP), 30% of India's habitation get less than 40 liters (L) per capita per day (lpcd), the amount required to maintain acceptable level of individual health and sanitation. Added to this are the problems of water quality, which is our focus here. Out of India's 11,274,819 documented sources of drinking water, by the year 2013-14, water quality testing data was available for only 1,734,882 (15.38%) (see http://indiawater.gov.in/IMISReports). Of the tested sites, 8% were found contaminated with chemical, bacteriological, or other contaminants beyond acceptable levels set by the NRDWP. Much of this contamination is attributable to sources of water, as 77% of India's population obtains its drinking water supply from sources other than piped water such as hand pumps, tube and dug wells, tanks, ponds, springs, canals, and rivers. The most vulnerable 10-14% population is reported to drink from uncovered and untreated water sources.

India recognizes water as a public good and access to safe water for drinking, cooking and other domestic as well as livestock use as a fundamental right. It employs an elaborate regulatory machinery for the provision, security, and safety of water that includes roles and responsibilities at national, state, district, sub district, and village levels. The regulatory framework also defines a role for healthcare workers, NGOs, and public-private partnerships. That being said, however, the demand for water quality management far exceeds the shear capacity for testing samples, and the resources and knowhow of the local communities to deal with the results of such testing. The NRDWP reports confess that for the skeleton infrastructure of Water Testing Laboratories available at the district level, it is simply impossible to meet the overall need to test the total 0.5 million water samples each year, if India were to meet the set target of once a year chemical and twice a year bacteriological test.

One of the key challenges in meeting this target is that accurate quantification of many contaminants requires analytical equipment which is not cost-effective to deploy at the sub-district level where routine testing occurs. In particular, trace contaminants such as arsenic, heavy metals, and pesticides require quantification via methods such as atomic adsorption spectroscopy (AAS), inductively coupled plasma-optical emission spectroscopy (ICP-OES), inductively coupled plasma-mass spectrometry (ICP-MS), or gas chromatography-mass spectrometry (GC-MS) in order to accurately detect contamination at their acceptable limits. These analytical instruments are present in state laboratory facilities, but require more capital investment and technical expertise than is available for district and sub-district laboratories. As a result, routine testing frequently quantifies only those contaminants which can be detected using the methods available at the district and sub-district level, with limited ability to identify harmful levels of those contaminants which require analytical equipment that is only available at the state level.

When one considers these constraints for India and other locations, one use case which would benefit for improved sampling technology is the collection of samples at local laboratories in a manner which makes them easy to transport to centralized laboratories with more advanced analytical equipment. While this is difficult to do with full-sized liquid samples due to their weight and the need for additional sample precautions such as acidification and/or temperature control, the ability to store contaminants in a solid matrix would facilitate easier transport between laboratories via methods such as the postal service. In addition to transfer between labs, the ability to store contaminants in a compact solid matrix would facilitate storage within laboratory facilities so that samples taken over time can be analyzed at a later date if the need emerges. This utility has already been demonstrated for medical diagnostics through the use of dried blood spot (DBS) testing, where blood samples are dried on a paper matrix, sent to centralized testing and storage facilities, and can be analyzed for small molecules and pathogens for as long as ten years. This ability to analyze samples of drinking water or other fluids at a different time or place would provide benefit to analytical applications in drinking water, environmental monitoring, and other applications.

SUMMARY OF THE INVENTION

According to one aspect of the invention, there is provided a device for collecting and releasing contaminants from water samples. The device includes at least one solid sorbent that is capable of adsorbing target contaminants, preserving the target contaminants for extended periods of time, and releasing the target contaminants for subsequent analysis. Means for supporting or containing the at least one solid sorbent and facilitating rapid adsorption of the contaminants is provided. A package stores the at least one solid sorbent with adsorbed contaminants.

According to another aspect of the invention, there is provided a device for collecting and releasing contaminants from fluid. The device includes at least one solid sorbent that adsorbs and releases target contaminants. Means for supporting or containing the at least one solid sorbent and facilitating rapid adsorption of the contaminants is provided. A package stores the at least one solid sorbent with adsorbed contaminants.

According to another aspect of the invention, there is provided a method of collecting and releasing contaminants from water samples. The method includes providing a water sampling device having at least one solid sorbent, and exposing the device to a sample of water. Also, the method includes allowing the at least one solid sorbent to adsorb one or more contaminants from the water, and removing the device from contact with the water. Furthermore, the method includes releasing the one or more contaminants from the at least one solid sorbent at a later time, and performing analysis on the released contaminants.

BRIEF DESCRIPTION OF THE DRAWINGS

FIGS. 6A-6B are scanning electron microscopy (SEM) images illustrating the granular morphology and surface morphology of iron oxide xerogels, where the xerogels are synthesized via epoxide-assisted gelation using a metal chloride precursor (either iron(III) chloride hexahydrate or aluminum(III) chloride hexahydrate) dissolved in ethanol before the addition of an epoxide (propylene oxide), followed by gelation and drying at room temperature for 18 days before sputtering with gold and imaging via SEM;

DETAILED DESCRIPTION OF THE INVENTION

Figure 1:
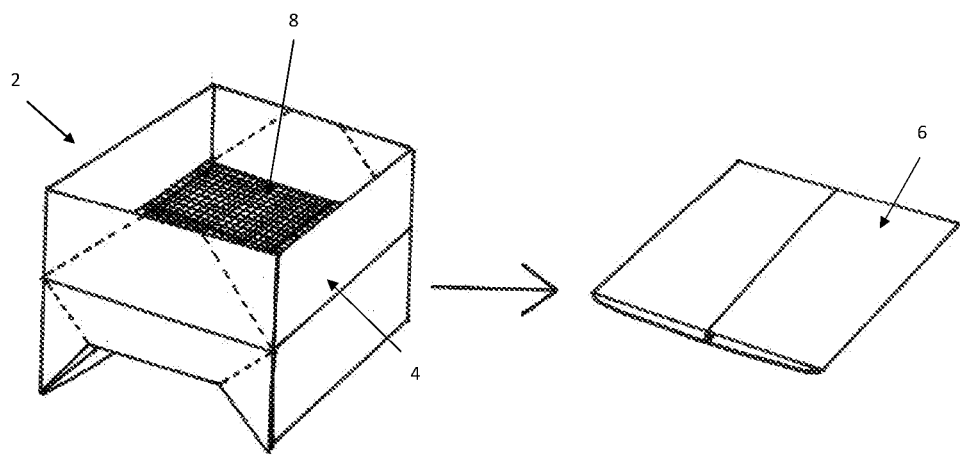
FIG. 1 is schematic diagram illustrating a foldable container structure used in accordance with the invention to collect contaminants.

The invention describes a water quality monitoring paradigm using sampling technology, materials, and system-level protocols to enable dry sample preservation of water samples to facilitate easy ambient-temperature shipping, storage, and rapid processing at centralized laboratories to greatly improve the ability to monitor the water quality. The ability to easily store and ship water samples has the potential to open a new paradigm in water quality management. Dry water sample preservation techniques described here are expected to facilitate easy shipping, storage, and rapid chemical and microbial analysis of water quality in centralized laboratories.

Several approaches can be conceived for dry preservation of water samples. Commercially available dried blood spot (DBS) sorbents already used for chemical and microbial analysis in human blood samples could be applied to water sample analysis. Custom-designed sorbents could also be used for this purpose. For example, membranes or porous media can be functionalized with positive charge using polyethyleneimine to bind negatively-charged bacteria when water is flushed through. In addition, high-surface-area inorganic morphologies such as silica or metal-oxide xerogels frequently present charged sites that may change charge with pH and redox conditions. Also, polymers containing stationary charged groups, such as ion exchange resins, can be used to adsorb positively or negatively charged species over a wide range of pH conditions. Water samples that are preserved in dry (or compact) state can then be analyzed using existing laboratory-based chemical and microbial analysis methods.

The key consideration in chemical preservation is to ensure a quantitative relationship between the concentration of analytes in original water sample and the laboratory results from the preserved sample. On one hand, strongly adsorbing sorbents may be used to facilitate concentration of the chemical during filtration across the sorbent. On the other hand, sorbents can provide a surface for chemicals to precipitate or crystallize out when water evaporates.

The water sample to be analyzed is flowed through or contacted by a porous sorbent, where the porosity and dimensions of the sorbent are designed to ensure adsorption of the analytes of interest. It is well-known that the amount of analyte that can be adsorbed will depend on the nature of the sorbent, total surface area of the sorbent, volume of weight of the sorbent, volume of the water sample, concentration of the analyte, pH, and any competing species in the water sample. A greater amount of sorbent or greater surface area of sorbent will result in greater amount of analyte adsorption. Furthermore, the diffusion and adsorption kinetics of the analyte will influence the amount adsorbed. Therefore, the porosity and dimensions (e.g. thickness or cross-section area) of the sorbent can be tuned to control the flow rate (for example, driven by gravity) and the sorbent surface area to achieve rapid adsorption. Examples of sorbents include cellulose (including filter paper) and surface modified cellulose (including cellulose nitrate and amidoximated cellulose), synthetic polymers such as polyamide, polyacrylamide and polyacrylonitrile, cation or anion ion exchange resins made of polystyrene-divinylbenzene or polyacrylic acid, chitin and chitosan, zeolites, mineral clays, lignin, xerogels with metal-oxide or silica backbone, activated carbon, carbon nanotubes, and composites of these materials.

Figure 7:
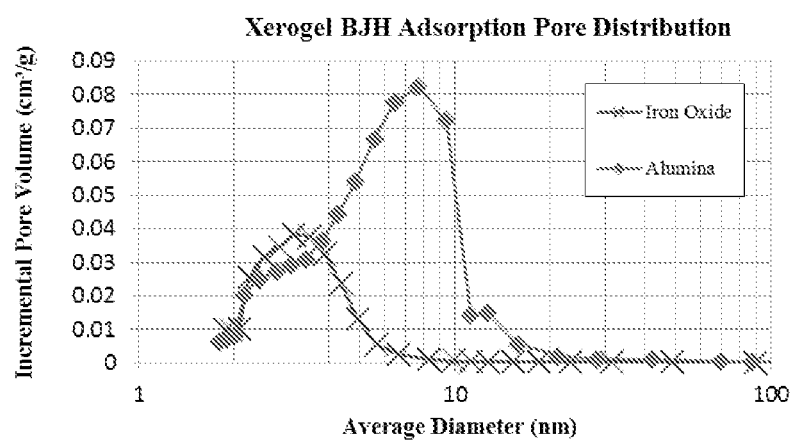
FIG. 7 is a graph illustrating the Barrett-Joyner-Halenda (BJH) pore size analysis of iron oxide and alumina xerogels, where the xerogels are synthesized via epoxide-assisted gelation using a metal chloride precursor (either iron(III) chloride hexahydrate or aluminum(III) chloride hexahydrate) dissolved in ethanol before the addition of an epoxide (propylene oxide), followed by gelation, five solvent exchanges in ethanol, drying for at least seven days at room temperature, and drying for three days at 130 degrees Celsius (° C.) to remove any residual moisture before BJH analysis via nitrogen adsorption and desorption.

As an explicit example of these sorbents, FIG. 6A-6B shows the granular morphology and surface morphology of iron oxide xerogels, as imaged by scanning electron microscopy (SEM). Xerogels are high surface area, nanoporous materials which can be easily and cheaply synthesized from precursor salts via epoxide-assisted gelation. Surface area and pore size distribution of fabricated iron oxide and alumina xerogels can be determined using Brunauer-Emmett-Teller (BET) and Barrett-Joyner-Halenda (BJH) analysis, as shown in FIG. 7. The surface area of the fabricated iron oxide xerogels is 330 square meters per gram of xerogel ($m^2/g$), while the alumina xerogels have a surface area of 460 $m^2/g$.

In many cases, complete adsorption of the analyte or analytes of interest can be desirable, but in some cases partial adsorption can be sufficient provided that it is consistent and a calibration can be established to relate the analyte concentration in the water sample to the amount adsorbed. Furthermore, given that certain conditions such as pH can affect analyte adsorption, chemicals (e.g. buffer) may be added to the water sample or incorporated into the device or sorbent to facilitate adsorption. Additionally, sensors that measure pH, turbidity, conductivity or other parameters may be incorporated in the device to provide additional information for device operation and monitoring purposes. Other mechanisms that are known to promote adsorption of different species on surfaces can also be used; for example, it is well-known that charged species can be adsorbed on electrodes under the application of an electric potential, such as that used in capacitive deionization method for water desalination. In some cases, sorption in solids or liquids (which may be encapsulated in a matrix in the form of droplets) can be used instead of surface adsorption. For example, hydrophobic organic species in water can preferentially partition into oil or into some polymeric substances such as poly(dimethyl siloxane). Alternatively, adsorption (or sorption) may be achieved by immersing a sorbent material into a water sample, with or without stirring, for a sufficiently long period of time.

Figure 5:
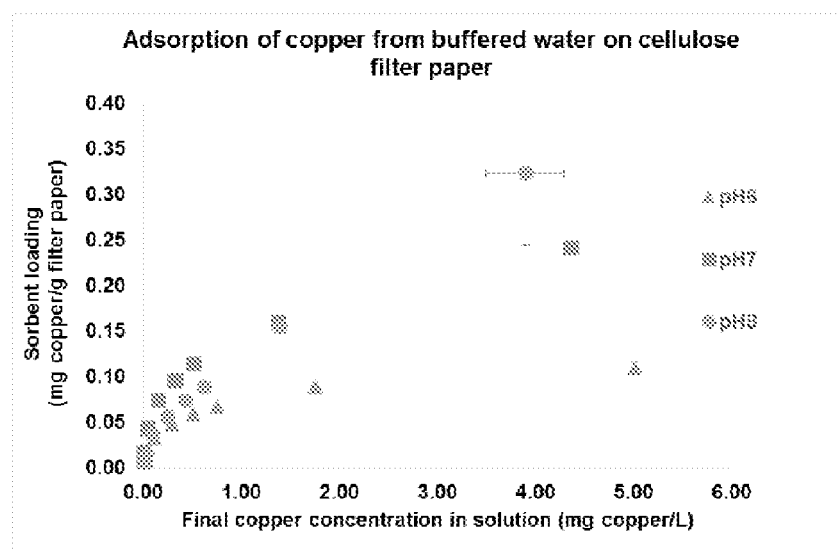
FIG. 5 is a graph illustrating the adsorption isotherms of copper on cellulose, from experiments in which copper at various concentrations from 0.025 mg/L to 5 mg/L was adsorbed from 30 mL of pH buffered deionized water using 0.15 g GE Whatman Grade 1 Qualitative filter paper.
Figure 8:
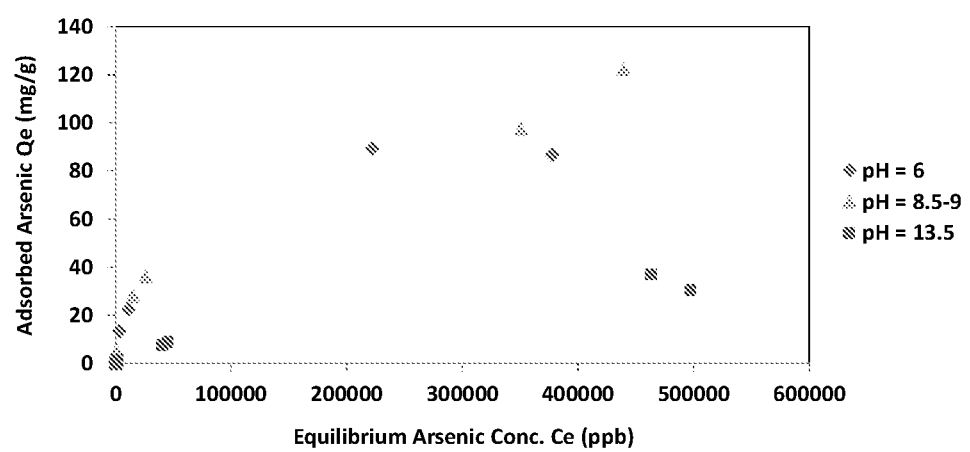
FIG. 8 is a graph illustrating the adsorption isotherms of arsenic(III) on iron oxide xerogel at neutral and basic pH values, from experiments in which arsenic(III) (in the form of sodium arsenite) at various arsenic concentrations from 0.05 mg/L to 500 mg/L was adsorbed from 30 mL samples (with pH values modified via the addition of sodium hydroxide) onto iron oxide xerogels with sorbent masses from 23 to 102 mg (average mass 51 mg) over an adsorption period of at least 24 hours.

After adsorption is completed either by flowing the water sample through, by immersion, or any other means, the sorbent can be dried, or the residual water sample can be discarded, while retaining the desired analyte(s) on or in the sorbent. The sorbent may or may not be dried to remove water, stored, or transported to a different location. It is noted that the weight or volume of the sorbent (and any device the sorbent can be incorporated in) is less than that of the original water sample. By selecting materials with high adsorption capacities, the amount of sorbent needed for sampling is minimized. For example, commercial filter paper can adsorb 0.6 milligram (mg) copper per gram (g) of filter paper, as shown in FIG. 5, whereas cation exchange resins can exchange 2 moles of charge per liter of resin, which corresponds to different amounts of heavy metal cations depending on their charge. Due to their high surface area, iron-oxide xerogels reliably adsorb high amounts of arsenic at neutral pH (pH=6-9), with arsenic capacities as high as 120 mg per g xerogel sorbent, as shown in in FIG. 8, As a result, heavy metal cations from a 1 L water sample can be preserved on a sorbent such as a filter paper weighing 1 g to 10 g or ion exchange resins weighing 0.2 g to 10 g. Arsenic can be preserved from a 1 L water sample using xerogels weighing 0.1 g to 5 g. To retrieve the original concentration of analyte(s), the sorbent can be directly analyzed using methods that accept the sorbent without further processing (e.g. X-ray Fluorescence (XRF), X-ray Photoelectron Spectroscopy (XPS), graphite-furnace atomic absorption spectroscopy (GFAAS), laser ablation mass spectrometry (LA-MS), laser-induced breakdown spectroscopy (LIBS), or elemental analysis following chemical and/or microwave digestion.

Figure 9:
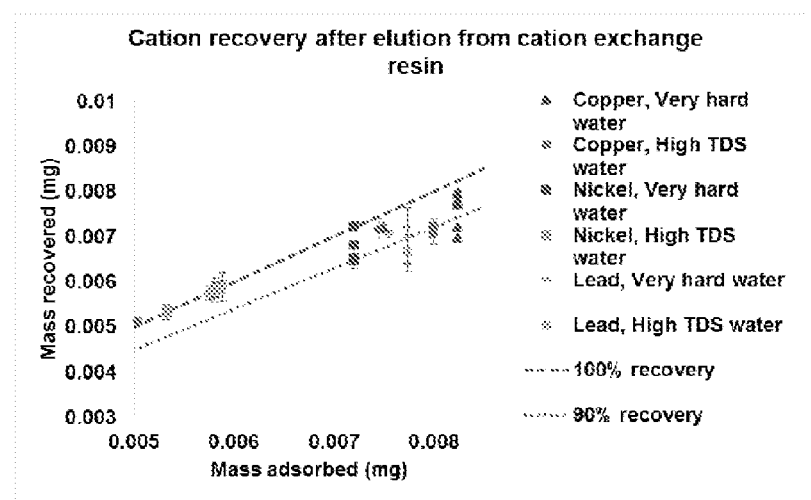
FIG. 9 is a graph illustrating the recovery of copper, nickel and lead from DOWEX G-26 ion exchange resin (commercially available from Dow Chemical Company) after dry storage for up to 4 months. Various amounts of resin, from 0.5 g to 3 g of resin were contacted with 250 L of water with 400 mg/L or 3200 mg/L total dissolved solids and 0.250 mg/L each of copper, nickel and lead. After adsorption, resin was blotted dry and allowed to dry at room temperature. After a certain time of dry storage, cations were eluted from the dry resin samples using 5 or 10% hydrochloric acid and the concentration of recovered cations was measured using ICP-OES
Figure 10:
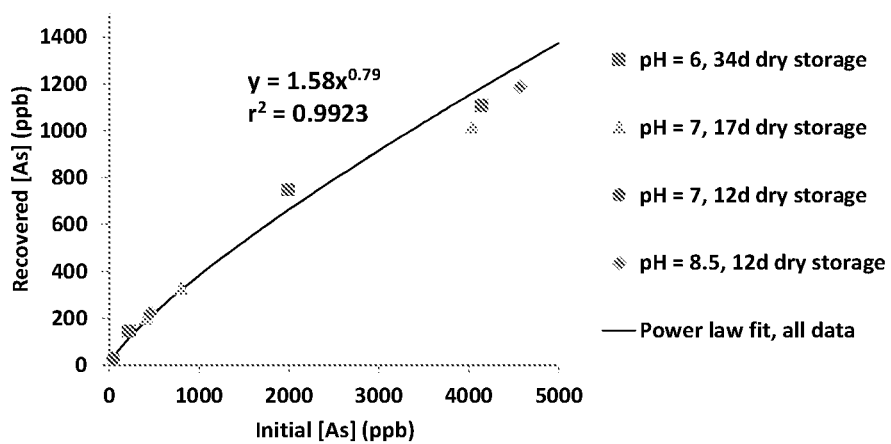
FIG. 10 is a graph illustrating the recovered arsenic concentration as a function of the initial arsenic sample concentration for iron oxide xerogels adsorbing arsenic(III) at neutral pH and desorbing the sampled arsenic at high pH, where arsenic(III) (in the form of sodium arsenite) was adsorbed from 30 mL samples onto iron oxide xerogels with sorbent masses from 38 to 61 mg (average mass 48 mg) over an adsorption period of at least 20 hours, dried and stored at room temperature for 12 to 34 days, and eluted from the dry xerogel samples via desorption into 30 mL of 0.1 molar (M) sodium hydroxide solution over a desorption period of 24 hours, with initial and recovered concentrations quantified via ICP-MS.

Alternatively, the analytes can be released into water or any liquid solution with controlled or known composition, so as to avoid interference with the analyte concentration measurement, such as deionized water, nitric, hydrochloric or sulfuric acid solution, or sodium hydroxide solution, with the desorbed analytes then quantified by use of methods such as ultraviolet/visible spectroscopy, flame atomic absorption spectroscopy (FAAS), ICP-OES, and ICP-MS. Examples of desorption methods include acidic pH dissolution of the sorbent (e.g. filter paper in nitric acid), acid pH elution (e.g. ion exchange resins in hydrochloric or nitric acid) or use of a pH where adsorption is no longer favorable (e.g. use of high-pH solutions such as sodium hydroxide to desorb anions from iron-oxide xerogels). For example, at least 80% of the amount of copper, lead or nickel adsorbed to ion exchange resins can be recovered from the sorbent after up to 4 months of dry storage at room temperature, as shown in FIG. 9. Similarly, the amount of arsenic recovered from iron-oxide xerogels after adsorption at neutral pH and desorption at high pH (by use of 0.1 M sodium hydroxide) follows a consistent power-law relationship over the entire concentration range of interest for drinking water samples (up to 5000 ppb) after dry storage periods of as long as 34 days at room temperature, as shown in FIG. 10. The amount or concentration of the analyte(s) measured by these methods can then directly correlate with the analyte concentration in the original water sample, or it can be related to the concentration of the analyte in the original water sample using calibration.

Similarly, dry or compact preservation of microbial contaminants can enable (1) direct culture of microbes for analysis and (2) nucleic acid (DNA/RNA) analysis. The process can involve concentration of the microbes by filtration or stirring and adsorption, or the use of cell lysis media to extract and adsorb nucleic acids or other biomolecules. For example, lysing the cells followed by filtering through a DNA-binding sorbent may be used to extract DNA and store it on the sorbent. The DNA can be released for analysis. Such sorbents and conditions to elute (remove) nucleic acids and other molecules are known, for example, for sorption and elution of DNA on silica.

Alternatively, bacteria can be captured using positively charged sorbents or filtered through a porous sorbent and the captured cells can be lysed (burst) before DNA analysis; for example, microbes could be captured in hydrogel matrices which facilitate their survival without allowing appreciable growth, such as methods that have been previously used for human cells. DBS cards and kits available for nucleic acid extraction and preservation may be adapted for analysis of water samples; for example, the FTA card marketed by GE Healthcare incorporates chemicals to lyse (burst) cells and bind their DNA, which can be preserved in dry state and is eluted upon exposing the card to water. Similarly, filtering or sorption may be used for preserving viable *E. coli* that can be cultured after dry or wet storage in a volume or weight that is smaller than that of the original sample. Preservatives may be added to the water sample or on the sorbent. For example, trehalose is a suitable preservative that retains high viability of *E. coli* after air-drying.

Materials for preservation of water samples can be integrated into cost-effective, easy-to-use devices that can be implemented for water monitoring paradigm in large-scale deployments.

Figures 11A, 11B:
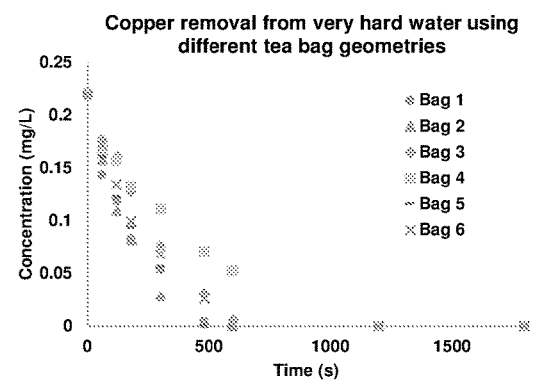
FIGS. 11A-11B is a table and graph illustrating the adsorption kinetics of copper onto DOWEX G-26 cation exchange resin contained in different tea bag geometries made of propylene meshes and flexible epoxy adhesive. After fabrication, bags were held stationary in 250 mL of stirring water with hardness 400 mg/L and 0.250 mg/L each copper, nickel and lead. Samples of solution were removed over the course of the experiment and the samples were analyzed using ICP-OES to generate concentration versus time curves for comparison of tea bag performance.

Sorbents are molded into a geometry or contained in a device, whose geometry is optimized for fast contaminant absorption kinetics, for device operation time on the order of 10 minutes or less. Optimal geometries for rapid uptake may differ depending on the sorbent and so different geometries may be used for different sorbents. Additionally, any material used in the device must be compatible with the entire adsorb/store/release protocol. For example, kinetics of copper uptake on ion exchange resins contained in polypropylene tea bags are negatively affected by the particle size of ion exchange resin; however, the opening size of the polypropylene mesh does not affect the kinetics significantly with all copper adsorbed within 10 minutes, as shown in FIGS. 11A-11B.

These devices should include the capability for collection of a prescribed volume of water, and reuse for repeated collections without cross-contamination. This includes use of containers with set or marked volumes, and a disposable sorbent that may be removed from the container and shipped to a laboratory for analysis, with a new sorbent inserted for the next water sample. The sorbent can include filter paper, xerogels, polymers, or composites. Also, the sorbent can be of the form of a packed-bed cartridge containing sorbent granules, a cartridge containing the sorbent coated onto a monolithic structure such as a honeycomb for well-defined flow, a rigid wafer consisting of a porous matrix impregnated with sorbent particles, a rigid wafer consisting of a porous matrix coated with a conformal layer of sorbent, a membrane consisting of a flexible matrix (such as paper or fabric) coated with a layer of additional sorbent, or a membrane consisting of a flexible matrix (such as paper or fabric) impregnated with sorbent (as particles or a coating), where the shape of the flexible matrices may be maintained during sample collection and shipping via a rigid support around the edges of the flexible matrix.

The inventive device includes the active sorbent material, which takes up the contaminants from solution, and any supporting structure necessary for device operation and maximum interaction between the sorbent surface and sample solution. The device can include multiple sorbents, each specific for the uptake of a specific contaminant or class of contaminants (for example, cationic, anionic, and organic contaminants). The sorbents may be mixed together, or they may be modularly contained to allow for detachment of one type of sorbent and separate storage, transport, release, and/or analysis of each contaminant. All materials contained in the device are compatible with the entire sampling and preservation protocol.

The device is contained in clean packaging, such as an envelope or small thin box. When ready for use, the user removes the device from the packaging and applies the water sample to the device following an established protocol for the specified time. The device may then be blotted of excess water using clean absorbents and/or dried at room temperature, after which the device is deposited back in the original or specifically provided packaging for clean long term storage and/or transportation. Additionally, if the device does not need to be dried prior to storage and/or transportation, the device may be directly deposited in the appropriate packaging without drying or blotting.

FIG. 1 shows a foldable container 2 that can be compacted for transport, shipped in an envelope, or fold into a shippable container itself used as a dry sampling device. Here, the container 2 (or other structure, e.g. a sheet or spiral) can be placed in a first configuration 4, such that a larger surface area is exposed to the water during the collection step. In the first configuration 4, the exposed area to the water includes a solid sorbent 8 used to collect contaminants. Then, the container 2 would be transformed to a second configuration 6 after sample collection encapsulating the sorbent 8, such that its included volume is substantially smaller than the first configuration 4 and therefore is more suitable for transport to a second location such as a centralized testing facility. Embodiments of such a container 2 include a paper 'cell' which can collapse to a near-flat packing; a creased sheet (e.g., a miura-ori pattern) that can be unfolded into a container containing water and then folded for transport.

Therefore, the transformable element 6 can also form the sample collection and capture container itself, or comprise a section of a container into which it is placed. Another embodiment would flow the water of other solution over and/or through the foldable element during the capture phase, and optionally later during the release phase.

Figure 2:
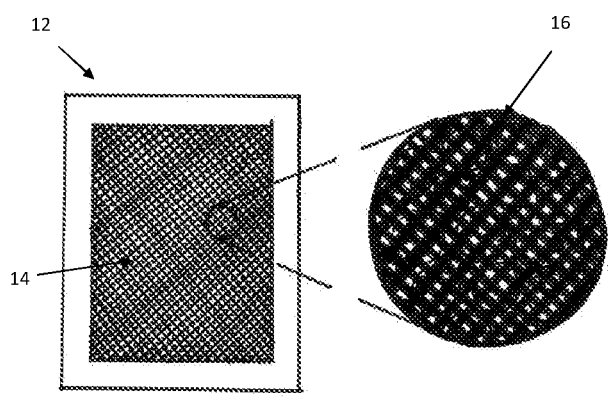
FIG. 2 is schematic diagram illustrating a tea bag arrangement used in accordance with the invention to collect contaminants.

FIG. 2 shows a tea bag arrangement 12 used in accordance with the invention. A tea bag 12, encloses the sorbent material 14. The tea bag 12 is fabricated from layers of plastic mesh or fabric 16, which are glued, melted or sewed together into a bag structure of an optimized geometrical shape that retains flexibility. The tea bag 12 may be fabricated from chemically inert materials such as polytetrafluoroethylene (PTFE) or polypropylene (PP) so that contaminant adsorption and release occurs consistently from the sorbent matrix 14 alone. The tea bag 12 can be either a free-standing structure, or have a handle or loop, which aids the user in using the tea bag to capture the contaminants. A single tea bag can contain multiple compartments for different sorbents.

In some embodiments, the sorbent support has a rigid or flexible handle, a string, or other mechanism of holding that enables the sorbent to be immersed, stirred in, or exposed to the water, such that the fingers of the operator do not touch the sorbent or the water sample and cause contamination.

Figure 3:
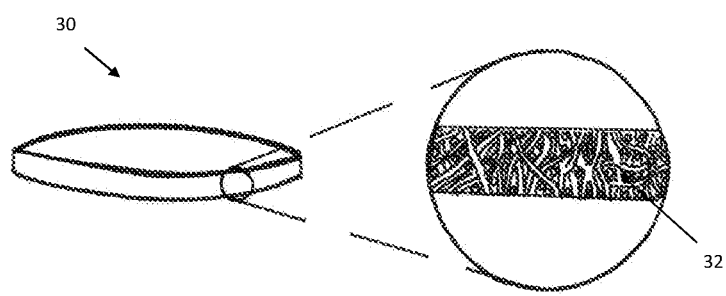
FIG. 3 is schematic diagram illustrating an impregnated rigid or flexible materials accordance with the invention to collect contaminants.

FIG. 3 shows an impregnated rigid or flexible materials arrangement 20 used in accordance with the invention. Impregnated rigid or flexible materials, in which the sorbent 32 is contained in the structure of the porous supporting material. Deposition of the sorbent material is achieved through direct chemical reaction, inclusion of the sorbent material during supporting material synthesis or adhesion using an appropriate adhesive. Supporting materials include synthetic filtration membranes, and filter paper sheets. The supporting material can already be in the desired geometry (such as a filter paper disk) prior to deposition, or the entire impregnated material can be synthesized in bulk and cut or molded into the desired geometry post synthesis, such as a fibrous brush, woven mat or porous monolith.

Figure 4:
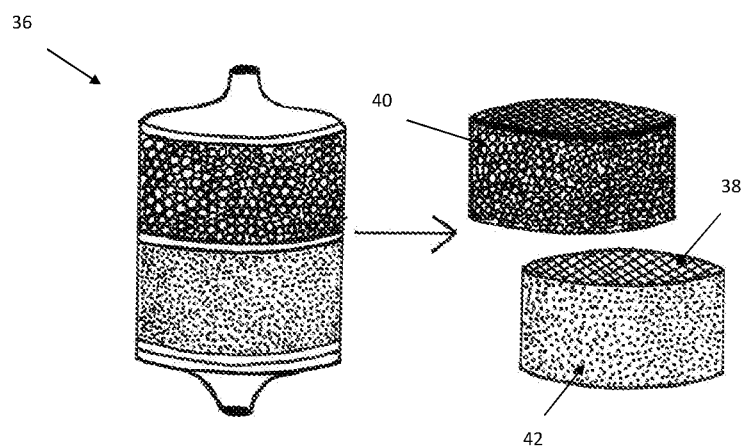
FIG. 4 is schematic diagram illustrating a packed bed geometry arrangement used in accordance with the invention to collect contaminants.

FIG. 4 shows a packed bed geometry arrangement 36 used in accordance with the invention. The packed bed geometry arrangement includes a layer 38 of sorbent that is contained between two porous supports 40, 42 in a cylindrical or rectangular geometry. The packed bed 36 can include multiple layers of sorbents, which can be taken apart and dried, transported and processed separately.

The sorbent material can include coated structures, such as plastic meshes, porous strips, fabrics, cotton or synthetic fibers, porous monolithic structures or honeycombs. The materials to be coated may be in their desired form prior to being coated or be coated in bulk, allowing for manipulation of the coated material into the desired geometry after processing, such as a fibrous brush or woven mat.

Also, the sorbent materials can be formed into other high-surface-area structures. The sorbent material makes up the majority of the device, such that these devices may or may not have significant supporting material, unlike the other embodiments aforementioned. Sorbents, such as polymers or xerogels, may be formed into structures during synthesis or molded/formed into a structure after synthesis. Examples include sorbent polymer fibers or films that are woven into a mat or fabric, or cut into short sections and fused together at one end in a brush format; polymers or xerogels that are cast into a mesh mold during synthesis; and materials that are melted and extruded into different geometries through electrospinning or 3D printing. These high-surface-area structures can consist solely of the sorbent material, or of composite materials incorporating the sorbent and other materials (such as chitosan or other polymers) which confer flexibility, toughness, or other desired mechanical properties to the structure.

Application of the water sample to these devices may occur through processes such as 1) flow of solution through the device, 2) flow of solution over the device, 3) stirring the device within the water sample, or 4) static adsorption by placing the device within the solution or the solution within the device. Additional supporting equipment necessary to using the sorbent can be included with the original packaging. Examples include rigid outer supports for sorbent impregnated, coated or formed membranes, foldable flow-through application systems in a cup or box form for use of flow through or flow over geometries (such as membranes or meshes) and a handle or frame for materials to be rigidly supported while being stirred with water samples.

Moreover, the invention provides the capability for filtering and spatially defined deposition of chemical and bacterial contaminants from the prescribed volume of water may be achieved by use of different sorbents in the same device connected to a single or multiple water containers within the device. The amount of water sampled by each sorbent may be controlled by appropriate choice of resistance to fluid flow (pressure divided by fluid flow rate) for the fluid flow pathways corresponding to each sorbent. A single-use sample collection "card" can be used by the invention, which receives the filtered/deposited constituents and can be mailed by post or the like. Also, there should be a requirement for only simple text or graphical instructions, and offering visual confirmation of successful use, and ease of distribution and collection of the samples. The invention could be fabricated using environmentally sustainable materials, and using local manufacturing capacities.

In other embodiments of the invention, the inventive device can include at least one of a pH sensor, a salinity sensor, a turbidity meter, a chromogenic sensor, or other kinds of sensor. Moreover, the time frame when removing the inventive device from the water to the analysis can range from 7-30 days. In addition, it can take between 3 and 15 minutes for the sorbent to absorb one or more contaminants from the water.

The invention reduces the cost and time limitations imposed by traditional water quality monitoring, by stably preserving contaminations in a compact and/or dry form, which can be shipped to the advanced labs using the existing postal service structure and associated fees. Dry preservation enables the transport of samples from a range of distances to advanced laboratories, allowing more water sources can be accurately analyzed for complete contaminant arrays using standard analytical techniques, potentially increasing the monitoring capabilities and reach of centralized bodies. Additionally, analysis protocols developed with the dry preservation technology complement the existing standard analytical procedures, so that the dry sampling technology aids the existing system.

Although the present invention has been shown and described with respect to several preferred embodiments thereof, various changes, omissions and additions to the form and detail thereof, may be made therein, without departing from the spirit and scope of the invention.

What is claimed is:

1. A method of collecting and releasing at least one target contaminant from a water sample, a volume, V, of the water sample picked as follows: 250 mL≤V≤1 L, the method comprising:

providing a water sampling device having at least one solid sorbent, wherein the at least one solid sorbent comprises a plurality of particles, and wherein size of each of the plurality of particles is picked to influence adsorption kinetics of the at least one target contaminant when the water sampling device is inserted in the water sample, wherein the size of the plurality of panicles are picked to be within the following range: 300 µm-650 µm;

exposing the device to the water sample;

allowing the at least one solid sorbent to: (1) adsorb the at least one target containment, (2) preserve the at least one target contaminant for extended periods of time, and (3) release the at least one target contaminant for subsequent analysis, wherein the at least one target contaminant is preserved in a compact or dry form, wherein a concentration, C, of the target contaminant is in the following range: 0 mg/L<C≤0.25 mg/L, the plurality of particles having size 300 µm-650 µm adsorbing all of the target contaminant within 20 minutes;

removing the water sampling device from contact with the water sample;

releasing the at least one contaminant from the at least one solid sorbent at a later time; and performing analysis on the released at least one contaminant.

2. The method in claim 1, wherein the device is packaged for storage or transportation before the release step.

3. The method as in claim 1, wherein the device dries after the removal step and before the release step.

4. The method as in claim 1, wherein the duration between the removal step and the analysis step is at least 24 hours.

5. The method as in claim 1, wherein the duration between the removal step and the analysis step is at least 7 days.

6. The method as in claim 1, wherein the duration between the removal step and the analysis step is at least 30 days.

7. The method in claim 1, wherein the at least one solid sorbent comprises at least one of an ion exchange resin, xerogel, or cellulose.

8. The method of claim 1, wherein the device is stored in a package to prevent contamination.

9. The method in claim 1, wherein the one more contaminant is adsorbed by manually stirring the device in the water sample.

10. The method in claim 1, wherein the one or more contaminants are adsorbed by flowing the water sample through the device.

11. The method in claim 1, wherein the one or more contaminants are adsorbed by immersing the device in the water sample.

12. The method in claim 1, wherein the one or more contaminants are released by flowing a release solution through the device.

13. The method in claim 1, wherein the one or more contaminants are released by immersing the device in a release solution.

14. The method of claim 1, wherein the one or more contaminants adsorption step requires less than 15 minutes.

15. The method of claim 1, wherein the one or more contaminants adsorption step requires less than 3 minutes.

16. The method in claim 1, wherein the device is transported to another location after adsorption for storage or analysis.

17. The method in claim 16, wherein the device is transported via the postal service or a commercial shipping service.

18. The method in claim 1, wherein the device is stored at the same location after adsorption for analysis at a later date.

19. A method of collecting and releasing at least one target contaminant from a fluid sample, a volume, V, of the fluid sample picked as follows: 250 mL≤V≤1 L, the method comprising:

providing a fluid sampling device containing at least one solid sorbent, wherein the at least one solid sorbent comprises a plurality of particles, and wherein size of each of the plurality of particles is picked to influence adsorption kinetics of the at least one target contaminant when the fluid sampling device is inserted in the fluid sample, wherein the size of the plurality of particles are picked to be within the following range: 300 µm-650 µm;

exposing the device to the fluid sample;

allowing the at least one solid sorbent to:

(1) adsorb the at least one target containment, (2) preserve the at least one target contaminant for extended periods of time, and (3) release the at least one target contaminant for subsequent analysis, wherein the at least one target contaminant is preserved in a compact or dry form, wherein a concentration, C, of the target contaminant is in the following range: 0 mg/L<C≤0.25 mg/L, the plurality of particles having size 300 µm-650 µm adsorbing all of the target contaminant within 20 minutes;

removing the fluid sampling device from contact with the fluid sample;

releasing the at least one target contaminant from the at least one solid sorbent; and performing analysis on the released at least one target contaminant.

20. A method for collecting and releasing at least a first target contaminant and a second target contaminant from a water sample, a volume, V, of the water sample picked as follows: 250 mL≤V≤1 L, the method comprising:

(a) providing a water sampling device fabricated from a mesh or a fabric, the water sampling comprising at least a first compartment and second compartment;

(b) providing a first solid sorbent enclosed within the first compartment, the first solid sorbent capable of adsorbing a first target contaminant;

(c) providing a second solid sorbent enclosed within the second compartment, the second solid sorbent capable of adsorbing a second target contaminant;

(d) exposing the water sampling device to the water sample;

(e) allowing the first solid sorbent enclosed within the first compartment to: (1) adsorb the first target contaminant, (2) preserve the first target contaminant for extended periods of time, and (3) release the first target contaminant for subsequent analysis, wherein the first target contaminant is preserved in a compact or dry form, wherein a first concentration, C1, of the first target contaminant is in the following range: 0 mg/L<C1≤0.25 mg/L;

(f) allowing the second solid sorbent enclosed within the second compartment to: (1) adsorb the second target contaminant, (2) preserve the second target contaminant for extended periods of time, and (3) release the second target contaminant for subsequent analysis, wherein the second target contaminant is preserved in a compact or dry form, wherein a second concentration, C2, of the second target contaminant is in the following range of 0 mg/L<C2≤0.25 mg/L;

(g) removing the water sampling device from contact with the water sample;
(h) releasing the first and second target contaminants from the first and second solid sorbents at a later time; and
(i) performing analysis on the released first and second target contaminants;
wherein the first solid sorbent comprises a first plurality of particles enclosed within the first compartment, and wherein size of each of the first plurality of particles is picked to influence adsorption kinetics of the first target contaminant when the device is inserted in the water sample,
wherein the second solid sorbent comprises a second plurality of particles enclosed within the second compartment, and wherein size of each of the second plurality of particles is picked to influence adsorption kinetics of the second target contaminant when the device is inserted in the water sample,
wherein the size of the first plurality of particles or the size of the second plurality of particles are picked to be within the following range: 300 μm-650 μm, and
the first plurality of particles of size 300 μm-650 μm in the first compartment adsorbing all of the first target contaminant within 20 minutes and the second plurality of particles of size 300 μm-650 μm in the second compartment adsorbing all of the second target contaminant within 20 minutes.

21. The device of claim 20, wherein openings in the mesh are picked to be within the following range: 150 μm-400 μm.

22. The device of claim 20, wherein either the first solid sorbent or the second solid sorbent is an ion-exchange resin.

23. The device of claim 20, wherein the mesh is any of the following: a polypropylene (PP) mesh or a polytetrafluoroethylene (PTFE) mesh.

* * * * *